United States Patent [19]

Punja

[11] 4,195,033

[45] Mar. 25, 1980

[54] 1-ACETYL OR 1-CYANO-2(2,2-DICHLOROVINYL)-3,3-DIMETHYL CYCLOPROPANE

[75] Inventor: Nazim Punja, Wokingham, England

[73] Assignee: Imperial Chemical Industries Limited, London, England

[21] Appl. No.: 931,297

[22] Filed: Aug. 4, 1978

Related U.S. Application Data

[62] Division of Ser. No. 684,957, May 10, 1976, abandoned.

[30] Foreign Application Priority Data

May 16, 1975 [GB] United Kingdom .............. 20887/75
May 16, 1975 [GB] United Kingdom .............. 20889/75
Feb. 12, 1976 [GB] United Kingdom .............. 5599/76

[51] Int. Cl.$^2$ .................... C07C 49/26; C07C 121/46
[52] U.S. Cl. ................... 260/464; 260/343.6; 260/465.7; 260/544 Y; 260/586 R; 260/586 C; 260/593 H; 560/124; 562/506; 562/602
[58] Field of Search .............. 260/464, 586 R, 586 C, 260/465, 586 R

[56] References Cited

U.S. PATENT DOCUMENTS

| | | | |
|---|---|---|---|
| 3,658,879 | 4/1972 | Julia | 260/464 |
| 4,000,180 | 12/1976 | Punja | 560/124 |

FOREIGN PATENT DOCUMENTS 832278 2/1976 Belgium .
833278 3/1976 Belgium .

OTHER PUBLICATIONS

Hondo, "Japan Chemical Ass., The 31st Autumn Annual Meeting, Abstracts", vol. I, 4A04, p.58 (1974).
Elliott et al., Nature, Nature, vol. 244, pp. 456–457 (1973).
Farkas et al., Collection Czechoslav. Chem. Commun., vol. 24, pp. 2230–2236 (1959).

*Primary Examiner*—Dolph H. Torrence
*Attorney, Agent, or Firm*—Cushman, Darby & Cushman

[57] ABSTRACT

1-acetyl or 1-cyano-2(2,2-dichlorovinyl)-3,3-dimethylcyclopropane. These compounds are useful intermediates.

3 Claims, No Drawings

1-ACETYL OR 1-CYANO-2(2,2-DICHLOROVINYL)-3,3-DIMETHYL CYCLOPROPANE

This is a division of application Ser. No. 684,957 filed May 10, 1976 and now abandoned.

The present invention relates to a process for the preparation of valuable chemical intermediates.

2(2,2-Dichlorovinyl)-3,3-dimethylcyclopropane carboxylic acid is an important intermediate in the production of insecticides, including for example, 3-phenoxybenzyl 2(2,2-dichlorovinyl)-3,3-dimethylcyclopropane carboxylate. The preparation of 2(2,2-dichlorovinyl)-3,3-dimethylcyclopropane carboxylic acid has been described by Farkas et al (Collection Czechoslov. Chem. Commun., (1959), 24, pp 2230–2236) by the reaction of ethyl diazoacetate with 1,1-dichloro-4-methyl-1,3-pentadiene followed by hydrolysis of the resultant ethyl ester. This process is not suitable for large scale preparation of the acid because of the difficulties of working with ethyl diazoacetate, which is a substance which can explosively decompose unless the conditions are rigourously controlled, and which is believed to be a potent carcinogen.

We have now discovered that the above acid may be prepared by a process which does not involve the use of diazoacetate.

Accordingly the present invention provides a process for the preparation of a compound of formula:

$$CZ_2=CH-CH{\overset{\diagdown}{\underset{\diagup}{C}}}CH-Y \qquad (I)$$
$$\qquad\qquad CH_3 \quad CH_3$$

Wherein Y is acetyl, carboxyl, cyano, and, or, alkoxycarbonyl containing from 1 to 4 carbon atoms in the alkoxy moiety, and Z is chlorine or bromine, which comprises (a) the step of treating a compound of formula:

$$CH_2=CH-\underset{\underset{CH_3}{|}}{\overset{\overset{CH_3}{|}}{C}}-CH_2-X \qquad (II)$$

Wherein X is acetyl, carboxyl or cyano, with a tetrahalomethane of formula $CZ_2QR$, where Q and R are independently selected from chlorine and bromine provided that Q is always bromine when either of Z and R are bromine, in the presence of a free radical catalyst, and (b) the step of treating the compound of formula:

$$CZ_2R-CH_2-CH-\underset{\underset{CH_3}{|}}{\overset{\overset{Q\quad CH_3}{|\quad|}}{C}}-CH_2-Y \qquad (III)$$

obtained in step (a) with at least two molar equivalents of a base.

Although any tetrahalomethane of the formula $CZ_2QR$ wherein Z, Q and R are as defined above may be used, those which are particularly preferred are those which lead to compounds wherein Z is chlorine, for example carbon tetrachloride and bromotrichloromethane.

The reaction outlined in step (a) is free radical in nature and is carried out in the presence of a free-radical catalyst, which term includes a free-radical initiator such as irradiation with a suitable, e.g. Ultra violet, light source, as well as conventional chemical free radical catalysts such as for example benzoyl peroxide and azobisisobutyronitrile.

The reaction may conveniently be carried out using an excess of the compound of formula $CZ_2QR$ as a diluent, at temperatures in the range 50° C. to 100° C., preferably 80°–90° C., at periods from 1 to 20 hours.

The product of the reaction of step (a) is a compound of formula:

$$CZ_2R-CH_2-CH-\underset{\underset{CH_3}{|}}{\overset{\overset{Q\quad CH_3}{|\quad|}}{C}}-CH_2-X$$

wherein X, Z, Q and R are as defined above. Such compounds have not been previously described and are part of the present invention. Examples of such compounds are 4-bromo-3,3-dimethyl-6,6,6-trichlorohexanoic acid 3,3-dimethyl-4,6,6,6-tetrachlorohexanoic acid, 3-bromo-1-cyano-2,2-dimethyl-5,5,5-trichloropentane, 1-cyano-3,3-dimethyl-4,6,6,6-tetrachlorohexane, 4,4-dimethyl-5,7,7,7-tetrachloroheptan-2-one, and 5-bromo-4,4-dimethyl-7,7,7-trichloroheptan-2-one.

The compounds of formula:

$$CZ_2R-CH_2-CH-\underset{\underset{CH_3}{|}}{\overset{\overset{Q\quad CH_3}{|\quad|}}{C}}-CH_2-Y$$

are subjected in step (b) of the process to treatment with at least two moles of a base. This part of the process involves two separate stages, cyclisation and B-elimination of hydrogen halide, but it is not clear in what order these two stages proceed, or if they proceed simultaneously. The product of the process is a cyclopropane derivative of formula:

$$CZ_2=CH-CH{\overset{\diagdown}{\underset{\diagup}{C}}}CH-Y$$
$$\qquad\qquad CH_3 \quad CH_3$$

Suitable bases for carrying out the process include tertiary amines, for example pyridine, triethylamine, diethylaniline, N-methyl piperidine, and also alkali metal alkoxides, for example sodium methoxide, sodium ethoxide, and potassium t-butoxide. The step is conveniently carried out in a diluent or solvent for the reactant and the base. A particularly convenient manner of conducting this step is to heat a solution of the reactant in an alcohol corresponding to the alkali metal alkxoide being used as base for a period of from 1 to 20 hours.

When the process of the invention is applied to compounds of formula II where X is cyano or acetyl the direct product is a compound of formula I where Y is cyano or acetyl. These compounds are novel and as such form part of the present invention. Examples of particular compounds of this type include 1-cyano-2-(2,2-dichlorovinyl)-3,3-dimethylcyclopropane and 1- acetyl-2-(2,2-dichlorovinyl)-3,3-dimethylcyclopropane. The compounds of these types may be readily converted into the corresponding carboxylic acids by, for example, aqueous alkaline hydrolysis of the cyano group or by oxidation of the acetyl group with alkali metal hypochlorite. These processes are set out more fully in our copending U.K. Patent Applications Numbered 20896/75 and 20894/75 respectively.

When the process of the invention is however a compound of formula II wherein X is carboxyl the direct product is not the compound of formula I where Y is carboxyl, but the lactone of formula:

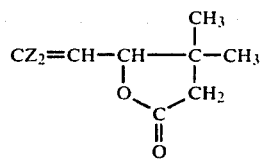

This lactone on treatment with for example an inorganic acid halide, for example a thionyl halide, phosphorus tri-or pentahalide or oxyhalide yields a product believed to be a compound of formula:

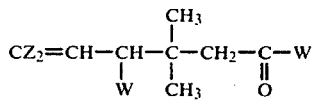

where W is halogen, and this product on treatment with at least two molar equivalents of a base which includes at least one molar equivalent of an alkali metal alkoxide containing from 1 to 4 carbon atoms yields a compound of formula I wherein Y is alkoxycarbonyl. These processes are more fully described in our copending UK Patent Applications numbered 20898/75 and 29253/75. The product of formula I wherein Y is alkoxycarbonyl may be hydrolysed using acid conditions e.g. hydrobromic or hydrochloric acid hydrolysis to yield the compound of formula I wherein Y is carboxyl.

The invention is illustrated by the following examples.

EXAMPLE 1

This example illustrates the preparation of 4-bromo-3,3-dimethyl-6,6,6-trichlorohexanoic acid.

3,3-Dimethylpent-4-enoic acid (7.2 g.) is stirred with bromotrichloromethane (40.0 g.) at 80° C. to 90° C. under a nitrogen atmosphere with periodic addition of benzoyl peroxide (0.5 g. in total) over a period of 10 hours. The excess bromotrichloromethane is removed by evaporation under reduced pressure and the residue recrystallised from petroleum ether (boiling range 60°-80° C.) and chloroform to yield 4-bromo-3,3-dimethyl-6,6,6-trichlorohexanoic acid identical with the product obtained in Example 2 below.

EXAMPLE 2

This example also illustrates the preparation of 4-bromo-3,3-dimethyl-6,6,6-trichlorohexanoic acid.

A mixture of 3,3-dimethypent-4-enoic acid (18.2 g.), carbon tetrachloride (100 ml.), bromotrichloromethane (57.0 g.) and benzoyl peroxide (0.15 g.) was refluxed under a nitrogen atmosphere for 72 hours after which the volatile portion was removed by evaporation under reduced pressure. The residue was recrystallised from petroleum ether (boiling range 80° to 100° C.) to yield 4-bromo-3,3-dimethyl-6,6,6-trichlorohexanoic acid, m.p. 123°-124° C.

EXAMPLE 3

By the use of the procedure illustrated in Example 1 the following compounds are prepared from the appropriate reactants thus:
3,3-Dimethyl-4,6,6,6-tetrachlorohexanoic acid from 3,3-dimethylpent-4-enoic acid and carbon tetrachloride, and
5-bromo-4,4-dimethyl-7,7,7-trichlorohept-2n-2-one from 4,4-dimethylhex-5-en-2-one and bromotrichloromethane.

EXAMPLE 4

This example illustrates the preparation of 3-bromo-1-cyano-3,3-dimethyl-5,5,5-trichloropentane.

A mixture of 1-cyano-2,2-dimethylbut-4-en (0.4 g.), bromo-trichloromethane (0.8 g.), carbon tetrachloride (2.0 ml.) and benzoyl peroxide (0.05 g.) was refluxed for a period of 8 hours after which it was cooled, diluted with carbon tetrachloride (5 ml.) and washed with saturated sodium bicarbonate solution and with water. After drying over anhydrous magnesium sulphate the solvent was evaporated under reduced pressure to yield 3-bromo-1-cyano-2,2-dimethyl-5,5,5-trichloropentane as a residual oil.

EXAMPLE 5

This example illustrates the preparation of 1-cyano-2-(2,2-dichlorovinyl)-3,3-dimethylcyclopropane.

A mixture of 3-bromo-1-cyano-2,2-dimethyl-5,5,5-trichloropentane (0.5 g.) and a solution of sodium (0.2 g.) in ethanol (10 ml.) is refluxed for 2 hours after which the ethanol is removed by evaporation under reduced pressure. The residue is partitioned between chloroform (20 ml.) and water (20 ml.) and the chloroform layer separated, washed with water and dried over anhydrous magnesium sulphate. Removal of the solvent by evaporation under reduced pressure yields 1-cyano 2-(2,2,-dichlorovinyl)-3,3-dimethylcyclopropane, identified by infra-red and nuclear magnetic resonance spectroscopy.

EXAMPLE 6

Using the procedure of Example 1 5-bromo-4,4-dimethyl-7,7,7-trichlorohept-2n-2-one is converted into 1-acetyl-3(2,2,dichlorovinyl)-2,2,dimethylcyclopropane.

EXAMPLE 7

This example illustrates the preparation of 5(2,2-dichlorovinyl)4,4-dimethyl-2-oxotetrahydrofuran.

4-Bromo-3,3-dimethyl-6,6,6-trichlorohexanoic acid (0.8 g.) was added to a stirred solution of sodium (0.2 g.) in dry ethyl alcohol (25 ml.) at the ambient temperature, and the mixture refluxed for 1 hour, during which time a white precipitate was formed. The ethyl alcohol was removed by evaporation under reduced pressure and residual material partitioned between chloroform (10 ml.) and water (25 ml.). The aqueous phase was separated, acidified with concentrated hydrochloric acid to pH 1, and extracted with petroleum ether (boiling range 40° to 60° C., 3×15 ml). The combined petroleum ether extracts were washed with water (10 ml.), dried over anhydrous sodium sulphate, and concentrated by evaporation of the solvent under reduced pressure. The residual oil was purified by preparative thin layer chromatography using silica on glass plates with a methanol (20% by volume) and chloroform (80% by volume) mixture as eluent. 5(2,2-Dichlorovinyl)-4,4-dimethyl-2-oxotetrahydrofuran was obtained as a colourless oil having an Rf ca. 0.8 in the above t.l.c. system, and characterised by mass spectroscopic and infra-red spectral examination (m/e 208).

EXAMPLE 8

This example illustrates the preparation of ethyl 2-(2,2,-dichlorovinyl)-3,3-dimethylcyclopropane carboxylate from 5-(2,2,-dichlorovinyl)-4,4-dimethyl-2-oxotetrahydrofuran.

A mixture of 5-(2,2-dichlorovinyl)-4,4-dimethyl-2-oxotetrahydrofuran (3.7 g.) and thionyl chloride (8.4 g.) was heated at the reflux temperature for 2.5 hours after which the excess thionyl chloride was distilled off at atmospheric pressure. When the mixture temperature reached 98° C. the distillation was discontinued and the residue cooled to 40° to 50° C. Ethanol (7.0 ml.) was added and the solution obtained added to a solution of sodium (0.85 g.) in ethanol (25 ml.) and the mixture stirred at the ambient temperature for 1 hour. The mixture was neutralised with aqueous hydrochloric acid, concentrated by evaporation under reduced pressure and the residue partitioned between water and toluene. After washing the toluene solution with water, it was dried over anhydrous magnesium sulphate and concentrated by evaporation under reduced pressure at 40° C. The liquid residue was shown by infra-red and nuclear magnetic resonance to comprise ethyl 2-(2,2-dichlorovinyl)-3,3-dimethylcyclopropane carboxylate in 82% yield. The product consisted of 25% of the cis-isomer and 75% of the trans-isomer.

I claim:

1. A compound of the formula:

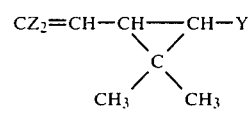

wherein Y is acetyl or cyano, and Z is chlorine.

2. 1-Acetyl-2(2,2-dichlorovinyl)-3,3-dimethylcyclopropane.

3. 1-Cyano-2-(2,2-dichlorovinyl)-3,3-dimethylcyclopropane.

* * * * *